(12) United States Patent
Becker et al.

(10) Patent No.: US 8,742,177 B2
(45) Date of Patent: Jun. 3, 2014

(54) CATALYST AND PROCESS TO PRODUCE BRANCHED UNSATURATED ALDEHYDES

(71) Applicants: Rohm and Haas Company, Philadelphia, PA (US); Dow Global Technologies LLC, Midland, MI (US)

(72) Inventors: Michael C. Becker, Dickinson, TX (US); Robert J. Olsen, Lansdale, PA (US); James F. Tate, New Castle, DE (US); Jose Antonio Trejo-O'Reilly, Lansdale, PA (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/708,183

(22) Filed: Dec. 7, 2012

(65) Prior Publication Data

US 2013/0172626 A1   Jul. 4, 2013

Related U.S. Application Data

(60) Provisional application No. 61/581,070, filed on Dec. 28, 2011.

(51) Int. Cl.
*C07C 45/65* (2006.01)
*B01J 8/00* (2006.01)

(52) U.S. Cl.
USPC ........................................... 568/459; 422/187

(58) Field of Classification Search
USPC ........................................ 568/459; 422/187
See application file for complete search history.

(56) References Cited

U.S. PATENT DOCUMENTS

| | | | |
|---|---|---|---|
| 3,037,052 A | 5/1962 | Bortnick |
| 3,422,148 A | 1/1969 | Wollner |
| 4,868,343 A | 9/1989 | King et al. |
| 5,434,313 A | 7/1995 | Harrison et al. |
| 5,841,002 A | 11/1998 | Harrison et al. |
| 2004/0138510 A1 | 7/2004 | Kramarz et al. |
| 2005/0004401 A1 | 1/2005 | Barnicki et al. |
| 2005/0277793 A1 | 12/2005 | Kawasaki et al. |
| 2005/0288533 A1 | 12/2005 | Barnicki et al. |
| 2008/0242899 A1 | 10/2008 | Oota et al. |
| 2011/0021845 A1 | 1/2011 | Zim et al. |

FOREIGN PATENT DOCUMENTS

| | | |
|---|---|---|
| JP | 08169854 | 7/1996 |
| JP | 2005118676 A | 5/2005 |
| JP | 2005281255 A | 10/2005 |
| JP | 2006028053 A | 2/2006 |

OTHER PUBLICATIONS

Cossu, et al, "No. 349. —Recherches sur les acroleines-2,3 disubstitueees", Bulletin de la Societe Chimique De France, Societe Francaise de Chimie, vol. 708, pp. 1887-1890 (1975).

*Primary Examiner* — Sikarl Witherspoon
(74) *Attorney, Agent, or Firm* — Carl P. Hemenway

(57) ABSTRACT

A continuous process and system for preparing branched aldehydes by reacting aldehyde with an acid polymeric catalyst absent any metal from Group VIII to produce a product having about 10 to 99.99% by weight branched unsaturated aldehyde and at least 92% selectivity of reaction to the branched aldehyde and recycling a portion of the product.

12 Claims, No Drawings

CATALYST AND PROCESS TO PRODUCE BRANCHED UNSATURATED ALDEHYDES

This invention relates to the use of catalysts in the production of branched aldehydes. In particular, this invention relates to the use of acid polymeric heterogeneous catalysts to make branched unsaturated aldehydes that can be, if desired, then hydrogenated to produce branched alcohols, or oxidized, if desired, to produce branched acids.

Branched, unsaturated $C_{2n}$ aldehydes may be synthesized from $C_n$ aldehydes using catalysts. In many applications, conversion of aldehydes is done via homogeneous catalysis using a base catalyst. As described in WO 93/20034, this involves a continuous process where the aldehyde, the catalyst, and water are reacted and then separated to produce an unsaturated, branched $C_{2n}$ aldehyde, water, $C_n$ aldehyde, and impurities. However, because the catalyst is homogeneous, some catalyst is purged with any by products such as water that must be purged from the system. For example, when n-butanal is used as the aldehyde feed for the production of 2-ethyl hexenal, in a system such as that described in WO 93/20034, the waste stream contains water, heavy byproducts, and sodium butyrate, a byproduct of the alkali catalyst. The sodium butyrate in this stream consumes the catalyst, adding cost, and is an undesirable impurity in the water; water treatment plants must be designed to handle this organic load, increasing costs. In addition, the water purge stream can be very large, resulting in an expensive water treatment requirement.

In other applications, conversion of aldehydes to alcohols is done via heterogeneous catalysis using a base or acid catalyst and a metal compound. For example, U.S. Patent Publication No. 2011/0021845 discloses alcohols prepared from aldehydes in the presence of an acidic or basic solid compound and a metal compound.

U.S. Pat. No. 3,037,052 discloses the use of a polymeric strong acid cationic macroreticular and gellular resins in hydrogen form as catalysts. The process used in the examples is a batch reaction of butanal to 2-ethyl hexenal. The '052 patent teaches that the macroreticular resins are very superior catalysts as compared to gellular catalysts. It is disclosed as a benefit that the macroreticular resins achieved improved selectivity and conversion and yield when compared to gellular strong acid cationic polymeric catalysts. However, the '052 patent obtains only an 85% selectivity to the desired product. The 15% loss to undesired products represents a significant economic penalty.

We have found that much improved selectivities can be obtained with certain macroreticular and gellular resins when operated under appropriate conditions. Therefore, the invention seeks to provide a more efficient heterogeneous catalyst that accomplishes the desired reaction while generating less waste. For instance, compared to WO 93/20034, in addition to the higher selectivities mentioned above, such a catalyst would allow for a process that eliminates the sodium butyrate from any water purge that must be taken, eliminating the need for water treatment.

In a first aspect of the invention, there is provided a continuous process for preparing branched unsaturated aldehydes comprising providing a feedstock with 5 to 99.9% by weight of a $C_n$ aldehyde, wherein n is 3 to 8; contacting the feedstock with a resin; reacting the mixture with the resin to produce an exit stream having 5 to 99.99% by weight branched unsaturated $C_{2n}$ aldehyde and at least 92% selectivity of reaction to the branched unsaturated $C_{2n}$ aldehyde; removing at least a portion of the branched unsaturated $C_{2n}$ aldehyde from the exit stream; and optionally recycling a portion of the exit stream to be reused in the feedstock. The resin has acid functional groups and does not have any metal from Group VIII of the Periodic Table of Elements.

In a second aspect of the invention, there is provided a system for preparing branched unsaturated aldehydes comprising a reactor that receives a feedstock with 5 to 99.9% by weight $C_n$ aldehyde, wherein n is 3 to 8, at an inlet; an exit stream that leaves the reactor; a separation zone that receives the reactor exit stream and separates at least a portion of the branched unsaturated $C_{2n}$ aldehyde from the reactor exit stream as a crude product; and an optional return line that recycles at least a portion of at least one of the remaining separation step exit streams to the reactor to be reprocessed in the reactor. The reactor has resin with acid functional groups absent any metal from Group VIII of the Periodic Table of Elements. The exit stream has 5 to 99.99% by weight branched unsaturated aldehyde and at least 92% selectivity of reaction to the branched unsaturated aldehyde.

In this aspect of this invention, the aldehyde product mixture is separated from the other components of the crude reaction mixture in which the aldehyde mixtures are produced by any suitable method. Suitable means of separation to be used in the separation zone include, for example, solvent extraction, crystallization, distillation, vaporization, wiped film evaporation, falling film evaporation, phase separation, and filtration.

As indicated above, during the process of this invention, the desired aldehydes may be recovered from the reaction mixture used in the process of this invention. For instance, in a continuous process the liquid reaction mixture (containing aldehyde product, etc.), i.e., reaction fluid, removed from the reaction zone can be passed to a separation step, e.g., distillation column, wherein the desired aldehyde product can be separated via distillation, in one or more stages, under normal, reduced or elevated pressure, from the liquid reaction fluid, and further purified if desired. The portion of the liquid reaction mixture that is not removed in the product stream from the separation step, containing aldehyde products, aldehyde feed, solvent, water, reaction byproducts, feedstock impurities, and the like, may then be recycled back to the reactor either in total or in part. Further separation of the components of the remaining liquid reaction mixture may also be desired by any of the separation means listed above, either in the same distillation column or in subsequent separation steps, for instance, water may be separated from the recycled liquid reaction mixture and purged from the system, as well as any other components in the stream that need to be purged from the system to avoid building up to an undesirable concentration in the reactor or the separation step. In general, if distillation is used as the separation means, it is generally preferred to separate the desired branched aldehydes from the reaction mixture under reduced pressure and at low temperatures to minimize the formation of undesirable byproducts during the separation process. However, the temperature and pressure used for this distillation separation is not critical to the invention and may be determined by anyone skilled in the art.

The invention is directed to a process for preparing branched unsaturated aldehydes by using resins, and preferably, acid polymeric heterogeneous catalysts, without generating sodium salts. The process is continuous. The $C_n$ aldehyde feedstock can be any aldehyde that, when reacted over an acidic catalyst, yields a longer-chain, branched aldehyde. Suitable reactant aldehydes include but are not limited to propanal, n-butanal, n-pentanal, 2-methylbutanal, 3-methylbutanal, hexanal, heptanal, octanal, longer chain aldehydes, and mixtures thereof. The preferred aldehydes are propanal, n-butanal, n-pentanal, 2-methylbutanal, 3-methylbutanal, hexanal, heptanal, and octanal, and mixtures thereof. The most preferred aldehydes include butanal, n-pentanal, 2-methylbutanal, and 3-methylbutanal, and mixtures thereof. Exemplary branched unsaturated aldehydes that may be produced include 2-ethyl hexenal from n-butanal and 2-propyl heptanol from n-pentanal.

As used herein, the terms hexanal, heptanal, and octanal include all isomers thereof.

Preferably, the feedstock has 5 to 99.9% by weight aldehyde. More preferably, the feedstock has 40 to 80% by weight aldehyde.

Preferably, the resin is provided as resin beads that are macroporous, gellular, or a combination of both. The term "gel" or "gellular" resin applies to a resin that was synthesized from a very low porosity (0 to 0.1 cm$^3$/g), small average pore size (0 to 17 Å) and low B.E.T. surface area (0 to 10 m$^2$/g) copolymer (measured by the B.E.T. (Brunauer, Emmett and Teller) method).

A macroporous resin is a resin that was synthesized from a copolymer having higher porosity and larger BET surface area than resins used for synthesizing gel resins.

Preferably, the resin beads are crosslinked, vinylaromatic polymer beads. These beads are surface functionalized with strongly acidic functional groups to a cation exchange capacity of from 0.1 to 4.0 meq/L.

The terms "surface functionalization" and "surface functionalized" are intended to refer to functionalized polymeric materials with a limited functionality which occurs at or near the surface of the polymer, and is not necessarily restricted to only the surface layer of aromatic nuclei. The depth of functionalization of the surface-functionalized catalyst beads is severely restricted, however, by limiting the functionality to 4.0 meq/L or less, and by functionalizing the beads in a manner that will promote functionalization from the surface inward, so that only the first few layers of aromatic nuclei are functionalized. Such functionalizations are known to those skilled in the art.

Preferred as monomers to be polymerized in making the crosslinked, vinylaromatic polymer beads are vinylaromatic monomers and polyvinylaromatic monomers. Vinylaromatic monomers have exactly one vinyl group per molecule. Polyvinylaromatic monomers have more than one vinyl group per molecule. Preferred vinylaromatic monomers are styrene, vinyltoluene, vinylnaphthalene, substituted versions thereof, and mixtures thereof. Preferred vinylaromatic monomers are styrene and α-methylstyrene. Small amounts, preferably less than 20% by weight of the monomers, of vinylaliphatic monomers may be present, but as these contain no functionalizable aromatic nuclei, they tend to reduce the overall catalytic activity of the surface-functionalized catalyst beads. More preferably, the amount of vinylaliphatic monomers is, by weight based on the total weight of monomer, 5% or less, more preferably 1% or less. Preferred are polymers made from monomer mixtures containing from 75 to 98 weight percent vinylaromatic monomers.

The polymer beads that result from polymerizing the monomer or mixture of monomers are crosslinked. This crosslinking comprises methylene bridges or other crosslinks that form during functionalization or other post-polymerization reactions, and it is preferably augmented by the introduction into the monomer mixture of crosslinking monomers, that is, those containing more than one polymerizable vinyl group. Preferred are polyvinylaromatic monomers, such as divinylbenzene, trivinylbenzene, divinylnaphthalene and the like, but one or more polyvinylaliphatic monomers may also be present as the crosslinking monomer, as for example ethylene glycol dimethacrylate, trimethylolpropane trimethacrylate and the like. Preferred polyvinylaromatic monomer is divinylbenzene. Crosslinking monomers may be introduced at levels from 1 to 100 weight percent of the total monomer. In the case of the crosslinked, polyvinylaromatic polymer beads that are made largely or entirely from crosslinking monomers, the preferred monomers are the polyvinylaromatic monomers described above. Preferred are polymers made from monomer mixtures containing from 2 to 25 weight percent polyvinylaromatic monomers.

The strongly acidic functional groups useful for functionalizing the vinylaromatic polymer beads to make the functionalized catalyst beads are preferably sulfonic acid groups and their salts. Methods for restricting functionalization to the surface of the polymer are known to those skilled in the art. Most of these depend upon the fact that a functionalizing agent, as for example sulfuric acid or chlorosulfonic acid, penetrates polymer beads from the surface at a regular rate, functionalizing aromatic nuclei as it penetrates, to create a shell of relatively uniform thickness in which the aromatic nuclei are largely or entirely functionalized. By proper choice of conditions, including the functionalizing reagent and whether and which swelling solvents are used, the rate at which the functionalizing agent penetrates and functionalizes the beads is kept slow enough that the penetration depth may be monitored. The functionalization is halted after it has proceeded to the desired depth, which is sufficient to produce a cation exchange capacity of from 0.1 to 4.0 meq/L, by quenching in water or by other methods which will be apparent to those skilled in the art. The sulfonated polymer, preferably, has a S/aromatic ring ratio (the molar ratio of sulfonic acid groups to aromatic rings) from 1/1000 to 2/1, and more preferably, has a S/aromatic ring ratio of between 0.5/1 to 2/1.

The formation of crosslinked, vinylaromatic polymer beads by suspension polymerization is well known to those skilled in the art. Formation of such beads containing macroporosity is similarly well known, and several approaches have been disclosed for preparing them.

Resins that are thermally stable and provide improved performance characteristics, including high selectivity, no or little degradation when used at high temperatures, and little or no reactor corrosion are preferred. Thermal stable resins are preferably chlorinated and tested at temperature ranges of 40 to 200° C.

The resin may have aromatic groups having more than one $SO_3H$ moiety and a polymer backbone. The resin may be polysulfonated monosulfonated, or undersulfonated. Polysulfonated resin has molar ratio of sulfonic acid groups to aromatic rings of more than 1/1. Monosulfonated resin has molar ratio of sulfonic acid groups to aromatic rings of 1/1. Undersulfonated resin has molar ratio of sulfonic acid groups to aromatic rings of less than 1/1. The phrase "sulfonic acid groups" includes both protonated and salt forms of the $SO_3H$ moiety.

The resin may be an interpenetrate resin. The resin is free of any metal from Group VIII, including iron (Fe), ruthenium (Ru), osmium (Os), and hassium (Hs), cobalt (Co), rhodium (Rh), iridium (Ir), meitnerium (Mt), nickel (Ni), palladium (Pd), platinum (Pt), and darmstadtium (Ds). As used herein, the term "metal" does not include alkali elements (column #1 of the periodic table of the elements) or alkaline earth elements (column #2 of the periodic table of the elements). Preferably, the resin is free of any metal. When it is said herein that the resin if free of a metal or that the metal is absent, it is meant that the amount of the metal in the resin is either zero or is less than 0.01% by weight based on the weight of the resin.

In one embodiment, the resin comprises a gellular resin having a particle size of 100 to 2000 μm and a particle size distribution that is Gaussian or Unimodal. If the particle size distribution is Gaussian, approximately 90 percent of the particles by number of particles have diameters within +/−100 micrometers of the median particle diameter size. A Unimodal particle size distribution is one in which the particles are of a generally uniform size. In a unimodal distribution, 90 percent of the particles by number of particles have diameters within +/−20 micrometers of the median particle diameter size. Resins that may be used in the process include organic acid functionalized polymers (e.g., Nafion® NR50 from E.I. du Pont de Nemours and Company, Wilmington, Del., and AMBERLYST™ resins and DOWEX™ resins from The DOW Chemical Company, Midland, Mich.).

The percent of solvent in the feedstock composition is, by weight based on the weight of the feedstock, 0 percent or more; preferably 10 percent or more; more preferably 20 percent or more; more preferably 30 percent or more. The percent of solvent in the feedstock composition is, by weight based on the weight of the feedstock, 95% or less; preferably, 80% or less; more preferably 60% or less; more preferably 40% or less.

Preferably, the solvent in the feedstock composition is not water and is unreactive in the reactor. More preferably, the solvent in the feedstock composition is one or more hydrocarbon; more preferably one or more aliphatic hydrocarbon; more preferably one or more alkane; more preferably one or more alkane having 4 to 12 carbon atoms; more preferably one or more alkanes having 6 to 10 carbon atoms.

Preferably, the feedstock is continuously fed to the reactor at a temperature of 40° C. or higher; more preferably 80° C. or higher; more preferably 100° C. or higher. Preferably, the feedstock is continuously fed to the reactor at a temperature of 200° C. or lower; more preferably 160° C. or lower; more preferably 130° C. or lower.

Preferably, the temperature in the reactor is 80° C. or higher; more preferably 100° C. or higher. Preferably, the temperature in the reactor is 200° C. or lower; more preferably 170° C. or lower; more preferably 130° C. or lower.

The aldehyde feedstock is reacted in a continuous reactor. Preferably, the continuous reactor is a packed bed column reactor or a continuous stirred tank reactor.

Among packed bed column reactors, the reactor preferably is a column having an aspect ratio of greater than 1. The column holds a packed bed of the resin. There may be one or more columns having packed beds used in the process. There may also be several passes made through the same or different columns to achieve a desired percentage of product yield. Exemplary columns include a tube reactor, loop reactor, capillary microreactor, gas-liquid two phase packed bed reactor, supercritical carbon dioxide reactor, microwave reactor, and bubble column reactor.

When a packed bed column reactor is used, feedstock containing aldehyde is passed through a packed bed of the resin. The packed bed may be washed with a solvent prior to adding the aldehyde. Solvents that may be used include chloroform, dichloromethane, tetrahydrofuran, dioxane, furane, diglyme, acetone, ethyl acetate, hexane, cyclohexane, pentane, heptane, iso-octane, n-octane, benzene, toluene, other hydrocarbons, oxygenated solvents, ethers, esters and mixtures thereof. Preferred solvents are hydrocarbons.

When a packed bed column reactor is used, the liquid hourly space velocity (LHSV) is, preferably, from 0.1 to 20 ($h^{-1}$), more preferably, from 0.5 to 10 ($h^{-1}$), and, most preferably, from 2 to 10 LHSV ($h^{-1}$). Preferably, the pressure is from 0.1 to 10 MPa and, more preferably, from 0.3 to 3 MPa.

Inert gas can be used to pressurize the reactor while running under continuous flow conditions, but it is not critical to the invention.

A continuous stirred tank reactor (CSTR) is a reaction vessel that has a means of agitation such as, but not limited to, a mechanical agitator; a continuous input feed stream; and a continuous output stream. Among embodiments using a CSTR, the CSTR is preferably operated at temperature of 40-200° C. and pressure 0.1 to 10 MPa.

When a CSTR is used, feedstock with aldehyde is passed through a continuously stirred tank reactor (CSTR) containing the resin catalyst. The resin catalyst may be washed with a solvent prior to adding the aldehyde. Solvents that may be used include chloroform, dichloromethane, methanol, ethanol, propanol, tetrahydrofuran, dioxane, furane, diglyme, acetone, ethyl acetate, pentane, hexane, cyclohexane, heptane, iso-octane, n-octane, benzene, toluene, cresol, hydrocarbons, oxygenated solvents, ethers, esters and mixtures thereof. Preferred solvents are hydrocarbons.

In the continuous reactor, the aldehyde reacts with the resin to produce an exit stream. Preferably, the exit stream has 5 to 99.99% by weight of the branched unsaturated aldehyde. More preferably, the exit stream has 30 to 99.99% by weight of the branched unsaturated aldehyde, and most preferably, the exit stream has 35-70% by weight of the branched unsaturated aldehyde.

In one preferred embodiment, 2-ethyl hexenal is produced from feedstock that contains butanal.

As used herein, conversion is $100*(1-(WAOUT/WAIN))$, where WAIN is the mass per unit time of aldehyde reactant in the feedstock at steady state, and WAOUT is the mass per unit time of unreacted aldehyde reactant in the output stream at steady state. Typical conversions in commercial processes are 10% to 100%. Higher conversion is desirable in general but is not critical to the present invention.

Selectivity is defined herein as $100*WEPA/WOTHER$, where WEPA is the mass of the product branched unsaturated aldehyde per unit time in the steady state output stream, and where WOTHER is the mass of all reaction products resulting from reactions of the reactant aldehyde per unit time in the steady state output stream, including the desired product branched unsaturated aldehyde. WOTHER does not include the mass of the unconverted reactant aldehyde and solvent charged in the feedstock. Preferably, selectivity is at least 92%; more preferably 95%

Preferably, the exit stream contains no organic sodium acid salt, such as sodium butyrate.

The exit stream preferably enters a separation zone, such as a distillation column, that separates the branched unsaturated $C_{2n}$ aldehyde as crude product and recycles at least a portion of at least one of the remaining separation zone exit streams to the reactor to be reprocessed in the reactor via a return line. The recycled stream, which may contain some branched unsaturated $C_{2n}$ aldehyde product, unreacted $C_n$ aldehyde feedstock, water, various impurities and inerts such as dissolved inert gases, and/or some solvent, can be combined with fresh feedstock and passed through the reactor. Water may also be produced by the reaction of $C_n$ aldehyde and the resin and may be separated from other streams by typical means and purged from the system. Preferably, some solvent and unreacted $C_n$ aldehyde is conveyed by a return line to be combined with the feed stream to the reactor.

The following examples are presented to illustrate the invention. In the examples, the following abbreviations have been used.

%-w is percent by weight;

Å is Angstrom;

C is centigrade;
cm is centimeter;
EPA is 2-ethyl hexenal;
g is grams;
Heavies are higher molecular weight products as compared to EPA;
kg is kilogram;
LHSV is liquid hourly space velocity;
m is meters;
meq is milliequivalents;
meq/L is volume exchange capacity in milliequivalents per liter of catalyst
meq/kg is weight exchange capacity in milliequivalents per kilogram of catalyst on a dry basis;
min is minutes;
ml is milliliters;
MPa is megapascals; and
sccm is gas flow rate in cubic centimeters per minute at standard gas conditions.
GL is a polystyrenic sulfonated gellular resin beads.
MR is a polystyrenic sulfonated macroreticular resin beads.
GC-MS is gas chromatographie coupled with mass spectroscopy.

Test Method

Gas Chromatography (GC Method) was used to separate volatile components of a mixture. A small amount of the sample to be analyzed was drawn up into a syringe. The syringe needle was placed into a hot injector port of the gas chromatograph, and the sample was injected. The injector is set to a temperature higher than the components' boiling points, so components of the mixture evaporated into the gas phase inside the injector. A carrier gas, such as helium, flowed through the injector and pushed the gaseous components of the sample onto the GC column. It is within the column that separation of the components took place. Molecules partitioned between the carrier gas (the mobile phase) and the high boiling liquid (the stationary phase) within the GC column.

EXAMPLES

In all the examples, the output streams were tested to discover whether any sodium salt was present; in all the examples, no sodium salt was observed.

Properties of Resin Catalyst Used:

| | | Resin Identification: | | | | | | | |
|---|---|---|---|---|---|---|---|---|---|
| | Units | MR1 | MR2 | MR3 | MR4 | MR5 | GL1 | GL2 | GL3 |
| Volume Exchange Capacity (VC) | eq/L | 1.7 | 1.9 | 0.7 | 1.95 | 3.6 | 0.7 | 1.15 | 1.35 |
| BET-Surface Area (SA) | m2/g | 53 | 50 | 80 | 35 | 28 | NR | NR | NR |

Example 1

Comparison of Macroporous Resin and Gellular Resin 30 ml of sulfonated polystyrenic catalysts (MR1, MR2, GL1 and GL2), provided by The Dow Chemical Company, Midland, Mich., was packed in a 1.58 cm internal diameter column flow-through a reactor. Butanal feedstock was used with a butanal quality of 97.7% purity and flowed through the reactor at 4 LHSV ($h^{-1}$) under inert gas pressure of 2 MPa and flowrate of 250 sccm. The temperature used was 80° C. Conversion and selectivity were measured by the GC method.

TABLE 1

Comparison of gellular and macroreticular resin. Conversion and Selectivity.

| Resin Identification | Type | Butanal Conversion %-w | 2-Ethyl hexenal (EPA) Selectivity %-w | RATIO: EPA/ Heavies |
|---|---|---|---|---|
| MR1 | Macroreticular | 30 | 85 | 3.2 |
| MR2 | Macroreticular | 29 | 86 | 3.0 |
| GL1 | Gellular | 29 | 93 | 6.6 |
| GL2 | Gellular | 31 | 94 | 6.5 |

The present invention provided excellent selectivity at usefully high conversion.

Example 2

Macroporous Resin with Low Volume Exchange Capacity 30 ml of sulfonated polystyrenic catalyst (MR3), provided by The Dow Chemical Company, Midland, Mich., was packed in a 1.58 cm internal diameter column flow-through reactor. Butanal feedstock was used with a butanal quality of 97.7% purity and flowed through the reactor at 4 LHSV ($h^{-1}$) under inert gas pressure of 0.7 MPa and flowrate of 50 sccm ($cm^3$/min). The temperature used was 80° C. Conversion and selectivity were measured by the GC method.

| Resin Identification | Catalyst Type | Butanal Conversion %-w | 2-Ethyl hexenal (EPA) Selectivity %-w | RATIO: EPA/ Heavies |
|---|---|---|---|---|
| MR4 | Macroreticular | 36 | 85 | 4.1 |

The present invention provided excellent selectivity at usefully high conversion.

Example 3

Gellular Resin and Low Butanal Feedstock Concentration Process 30 ml of sulfonated polystyrenic catalyst (GL3), provided by The Dow Chemical Company, Midland, Mich., was packed in a 1.58 cm internal diameter column flow-through reactor. Butanal solution was prepared by dilution in isooctane in 20/80 weight to weight ratio and used as a feedstock. The solution was then flowed through the reactor at 4 LHSV ($h^{-1}$) under inert gas pressure of 1 MPa and flowrate of 100 sccm (cm³/min). The temperature used was 130° C. Conversion and selectivity was measured by the GC method. GL3 is a gellular sulfonated polystyrenic resin catalyst.

| Resin Identification | Catalyst Type | Butanal Conversion %-w | 2-Ethyl hexenal (EPA) Selectivity %-w | RATIO: EPA/Heavies |
|---|---|---|---|---|
| GL3 | Gellular | 95 | 98 | 33 |

No sodium butyrate was detected using GC-MS method on the product from this reaction. The present invention provided excellent selectivity at usefully high conversion.

Comparative Example 4

Batch Process Stirred Reactor Results with (MR4)

Comparative Example in Batch

A stirred reactor was used for the catalyst application. 1 g of dried catalyst sample (MR4) and 5 ml of solution (55%-w/w butanal in isooctane) were charged into a small scale stirred reactor. The reactor was closed, nitrogen used to pressurize to 0.3 MPa and hold at 120° C. for 4 hours at 180 rpm. The reaction product was filtered and the liquid injected in gas chromatograph (GC).

| Resin Identification | Catalyst Type | Butanal Conversion %-w | 2-Ethyl hexenal (EPA) Selectivity %-w | RATIO: EPA/Heavies |
|---|---|---|---|---|
| MR4 | Macroreticular | 96 | 85 | 5.4 |

In this comparative example, selectivity was poor.

Example 5

Pentanal Feedstock Process to Make 2-Propylheptenal, or "Propyl Butyl Acrolein" ("PBA")

30 ml of sulfonated polystyrenic catalyst (MR4), provided by The Dow Chemical Company, Midland, Mich., was packed in a 1.58 cm internal diameter column flow-through reactor. Feedstock pentanal solution was prepared by dissolving pentanal (98%) in isooctane to make 80/20 weight (pentanal) to weight (solvent) ratio. The solution was then flowed through the reactor at 2 LHSV (h⁻¹) under inert gas pressure of 1 MPa and gas flowrate of 50 sccm (cm³/min). The temperature used was 120° C. Conversion and selectivity was measured by the GC method. MR4 is a macroreticular sulfonated polystyrenic resin catalyst.

| Resin Identification | Catalyst Type | Pentanal Conversion %-w | PBA Selectivity %-w | RATIO: PBA/Heavies |
|---|---|---|---|---|
| MR4 | Macroreticular | 60 | 93 | 10 |

No sodium pentanoic acid salt was detected using GC-MS method on the product from this reaction.

Example 6

CSTR

A laboratory made CSTR 3 reactor configuration connected in series could be used for this process. Each reactor volume would be 80 ml. Total catalyst charged would be 60 ml divided in three reactors with 20 ml in each one. MR4 catalyst would be used. Feedstock would be 55%-w/w butanal in isooctane. Flow rate used for the process would be 2 ml/min (2 LHSV) for the three reactor configuration. Pressure used for the process would be 0.5 MPa and temperature would be 120° C. Each reactor would be continuously stirred at 120 rpm. The process would be run for 12 hours. After the first 4 hours the product would be discarded and representative samples would be taken at 12 hours in the run at steady state condition. Samples would be taken to obtain conversion and selectivity by GC method.
Expected Results:

| Resin Identification | Catalyst Type | Butanal Conversion %-w | 2-Ethyl hexenal (EPA) Selectivity %-w | RATIO: EPA/Heavies |
|---|---|---|---|---|
| MR4 | Macroreticular | 60 | 97 | 28 |

The present invention would provide excellent selectivity at usefully high conversion.

What is claimed is:

1. A continuous process for preparing branched unsaturated aldehydes comprising:
   providing a feedstock with 5 to 90% by weight of a $C_n$ aldehyde, wherein n is 3 to 8;
   wherein the feedstock additionally comprises 10 to 95% solvent;
   contacting the feedstock with a resin, the resin having acid functional groups and absent any metal from Group VIII;
   reacting the mixture with the resin to produce an exit stream having 5 to 99.99% by weight branched unsaturated $C_{2n}$ aldehyde and at least 92% selectivity of reaction to the branched unsaturated $C_{2n}$ aldehyde;
   removing at least a portion of the branched unsaturated $C_{2n}$ aldehyde from the exit stream; and
   optionally recycling a portion of the exit stream to be reused in the feedstock.

2. The process of claim 1 wherein the resin comprises at least one of a macroporous resin and a gellular resin.

3. The process of claim 1 wherein the resin comprises a gellular resin having a particle size of 100 to 2000 μm and a particle size distribution that is either Gaussian or Unimodal or both, and wherein the gellular resin is selected from the group consisting of polysulfonated resins, monosulfonated resins, and undersulfonated resins.

4. The process of claim 1 wherein the contacting comprises continuously feeding the feedstock into a reactor at a temperature of 40 to 200° C. and a pressure of 0.1 to 10 MPa.

5. The process of claim 1 wherein the resin comprises an acid polymeric heterogeneous catalyst.

6. A system for preparing branched unsaturated aldehydes comprising:
   a reactor that receives a feedstock with 5 to 99.9% by weight $C_n$ aldehyde, wherein n is 3 to 8, at an inlet, the reactor having resin with acid functional groups absent any metal from Group VIII;

wherein the feedstock additionally comprises 10 to 95% solvent;

an exit stream that leaves the reactor, the exit stream having 10 to 99.99% by weight branched unsaturated $C_{2n}$ aldehyde and at least 92% selectivity of reaction to the branched unsaturated $C_{2n}$ aldehyde;

a separation zone that receives the reactor exit stream and separates at least a portion of the branched unsaturated $C_{2n}$ aldehyde from the reactor exit stream as a crude product; and optionally a return line that recycles at least a portion of at least one of the remaining separation step exit streams to the reactor to be reprocessed in the reactor.

7. The system of claim 6 wherein the resin comprises at least one of a macroporous resin and a gellular resin.

8. The system of claim 6 wherein the resin comprises a gellular resin having a particle size of 100 to 2000 μm and a particle size distribution that is either Gaussian or Unimodal or both, wherein the gellular resin is selected from the group consisting of polysulfonated resins, monosulfonated resins, and undersulfonated resins.

9. The system of claim 6 wherein the reactor comprises a packed bed reactor that is continuously fed with the feedstock and operates at a temperature of 40 to 200° C. and a pressure of 0.1 to 10 MPa.

10. The system of claim 6 wherein the reactor comprises a continuous stirred tank reactor, wherein the resin remains in the reactor; wherein the feedstock is continuously fed, and wherein the reactor operates at a temperature of 40~200° C. and a pressure of 0.1 to 10 MPa.

11. The process of claim 1 wherein the feedstock is contacted with the resin at a temperature of 100° C. or higher.

12. The system of claim 6 wherein the feedstock is contacted with the resin at a temperature of 100° C. or higher.

* * * * *